United States Patent [19]

Muhlenberg

[11] Patent Number: 5,819,740
[45] Date of Patent: Oct. 13, 1998

[54] SYSTEM AND METHOD FOR COMPRESSING DIGITIZED SIGNALS IN IMPLANTABLE AND BATTERY POWERED DEVICES

[75] Inventor: Lambert Muhlenberg, Landgraaf, Netherlands

[73] Assignee: Medtronic, Inc., Minneapolis, Minn.

[21] Appl. No.: 768,687

[22] Filed: Dec. 18, 1996

Related U.S. Application Data

[63] Continuation-in-part of Ser. No. 561,738, Nov. 25, 1995, abandoned.

[51] Int. Cl.⁶ ........................................... A61B 5/04
[52] U.S. Cl. ................................... 128/696; 607/9
[58] Field of Search ...................... 128/696; 364/715.02; 607/9, 59, 60

[56] References Cited

U.S. PATENT DOCUMENTS

| | | | |
|---|---|---|---|
| 4,449,536 | 5/1984 | Weaver | 128/696 |
| 4,503,510 | 3/1985 | Weaver | 364/715 |
| 4,567,883 | 2/1986 | Langer et al. | 128/696 |
| 4,633,884 | 1/1987 | Imai et al. | 128/696 |
| 4,920,489 | 4/1990 | Hubelbank et al. | 128/702 |
| 5,215,098 | 6/1993 | Steinhaus et al. | 128/702 |
| 5,217,021 | 6/1993 | Steinhaus et al. | 128/702 |
| 5,255,186 | 10/1993 | Steinhaus et al. | . |
| 5,312,446 | 5/1994 | Holschbach et al. | 607/9 |

FOREIGN PATENT DOCUMENTS

| | | |
|---|---|---|
| 0 583 490 A1 | 2/1994 | European Pat. Off. . |

OTHER PUBLICATIONS

Mueller, W., "Arrhythmia Detection Program For An Ambulatory ECG Monitor," University of Wisconsin Madison, ISBN 87664–405–1 —1978.

Ruttimann, Urs E., "Compression of the ECG by Prediction or Interpolation and Entropy Encoding," IEEE Transactions on Biomedical Engineering, vol. 26, No. 11, Nov. 1979.

Krishnakumar, A.S. et al., "Microprocessor–Based Data Compresson Scheme for Enhanced Digital Transmission of Holter Recordings," Computers in Cardiology, IEEE, 1961.

Abenstein, John P. et al., "A New Data–Reduction Algorithm For Real–Time ECG Analysis," IEEE Transactions on Biochemical Engineering, vol. BME–29, No. 1, Jan. 1982.

Reddy, B.R. Shankara et al., "ECG Data Compression Using Fourier Descriptors," IEEE Transations on Biomedical Engineering, vol. BME–33, No. 4, Apr. 1986.

Lynch, Thomas J., "Data Compression: Techniques and Applications," Electrocardiogram Compression.

Furht, Borivoje et al., "An Adaptive Real–Time ECG Compression Algorithm With Variable Threshold," IEEE Transactions on Biomedical Engineering, vol. 35, No. 6, Jun. 1988.

(List continued on next page.)

*Primary Examiner*—William E. Kamm
*Assistant Examiner*—George R. Evanisko
*Attorney, Agent, or Firm*—Michael J. Jaro; Harold Patton

[57] ABSTRACT

A system and method for more efficient data compression is provided, being particularly applicable to use in battery powered devices where there is a premium on minimizing the steps required and the amount of memory that must be dedicated to the task. The invention utilizes the technique of determining a delta or difference between each successive sample of the signal and the prior sample; examining the delta signals for a block comprising a predetermined number of such delta signals; determining the largest absolute delta value; determining the number of bits required to store such largest delta; and then storing both the determined number of bits and each delta value which is encoded with such determined number of bits. The block size is chosen to correspond to the type of signals being processed, and for typical medical applications is selected as a size within the range of 5–12 samples. The compressed data can be efficiently transmitted, such as from an implanted medical device to an external receiver, and decompressed by algebraically adding each delta to the value of the prior sample to recreate the respective samples and the signal.

20 Claims, 6 Drawing Sheets

OTHER PUBLICATIONS

Lamberti, C. et al., "Evaluation of Algorithm For Real–Time ECG Data Compression," IEEE, 1991.

Bedini, R. et al., "Performance Evaluation and Choice Criteria of Data Compression Algorithms By Extensive Test on CSE Data Base," IEEE 1991.

Zywietz, Chr. et al., "Compression of Diagnostic Resting Electrocardiograms," IEEE 1991.

SYSTEM AND METHOD FOR COMPRESSING DIGITIZED SIGNALS IN IMPLANTABLE AND BATTERY POWERED DEVICES

RELATED APPLICATION

This application is a continuation in part of the application of Muhlenberg Ser. No. 08/561,738 filed 25 Nov., 1995, abandoned entitled "System And Method For Compressing Digitized Signals In Implantable And Battery Powered Devices".

FIELD OF THE INVENTION

This invention relates to methods of compression of digitized signals, and in particular, compressing and decompressing digital data representative of physiological signals obtained by implantable or battery powered devices, so as to achieve efficient compression with relatively little data processing.

BACKGROUND OF THE INVENTION

In many medical applications there is a need to monitor on-going signals, and to digitize those signals and store the resulting data for later use. Particularly where an implantable or battery-driven device is employed, this task becomes difficult because of the need to conserve power, and to save memory. For example, an implantable pacemaker has a limited battery lifetime, and accordingly cannot dedicate large amounts of memory for storage of data, or utilize extensive processing techniques for complicated compression schemes. Where a task of the pacemaker is to sense, digitize and store intracardiac signals for later uploading to an external device, it is required to do this with a minimum of memory and processing. This leads to a requirement of efficient data compression which will provide significant reductions in bits to be stored, while minimizing the time involved in transferring data to the external device for processing and display. However, such a compression scheme cannot require severely complicated processing, both because of energy considerations and the amount of memory that would have to be dedicated to the software routine.

In any of the above applications where power and available memory are factors, there is a need for a relatively simple technique for gaining most of the available data compression, but for doing this without resorting to complex data processing. This invention achieves the aim of providing greater than 50% compression, while reducing the memory required for storage and the time for transporting the data. In addition to the implantable pacemaker embodiment, other applications include those involving digitized physiological signals such as ECG, EGM, respiration, blood pressure, etc.

SUMMARY OF THE INVENTION

It is a primary object of the invention to achieve a simple but efficient means and method for compression of signals, particularly signals representative of physiological parameters, for use with medical and other devices which have limited power available, such as implantable stimulators and other battery powered devices. Accordingly, there is provided a data compression and decompression technique based upon taking the time derivative between successive samples of a signal. The digital data for a predetermined block of successive samples, e.g. 5–12, is processed to determine the difference between the sample and the next prior sample, referred to as a delta value. When the deltas for a block have all been compiled, the delta with the largest absolute value is found, and it is determined how many bits (# bits) are required for that max delta. Then, the value of # bits and the bits for each delta in the block are stored successively, after which the technique is repeated for each block. Decompression is carried out by determining the # bits for each block, and integrating the signal by adding (or subtracting) the delta value to the value of each sample. The initial value (integration constant) as used in both compression and decompression is set to a fixed value, such as the value which represents a basal voltage of zero.

It has been found that the technique of this invention provides efficient compression of more than 50% for most medical-type signals, such as ECGs. This yields a similar reduction in required storage and transfer time. Although much more sophisticated compression methods are available, it is difficult to produce more than an other 5% or so compression, and at the cost of significant memory and processing. Further, the compression method of this invention is lossless, in that the original digital signal can be fully reconstructed. This contrasts with other methods such as adaptive delta pulse code modulation, which provides a greater compression ratio, but at the expense of some signal distortion. The method and apparatus of this invention thus provide a much needed compromise for many applications, including particularly the above-mentioned medical applications.

DESCRIPTION OF THE PREFERRED EMBODIMENT

Figures 1, 2A, 2B:
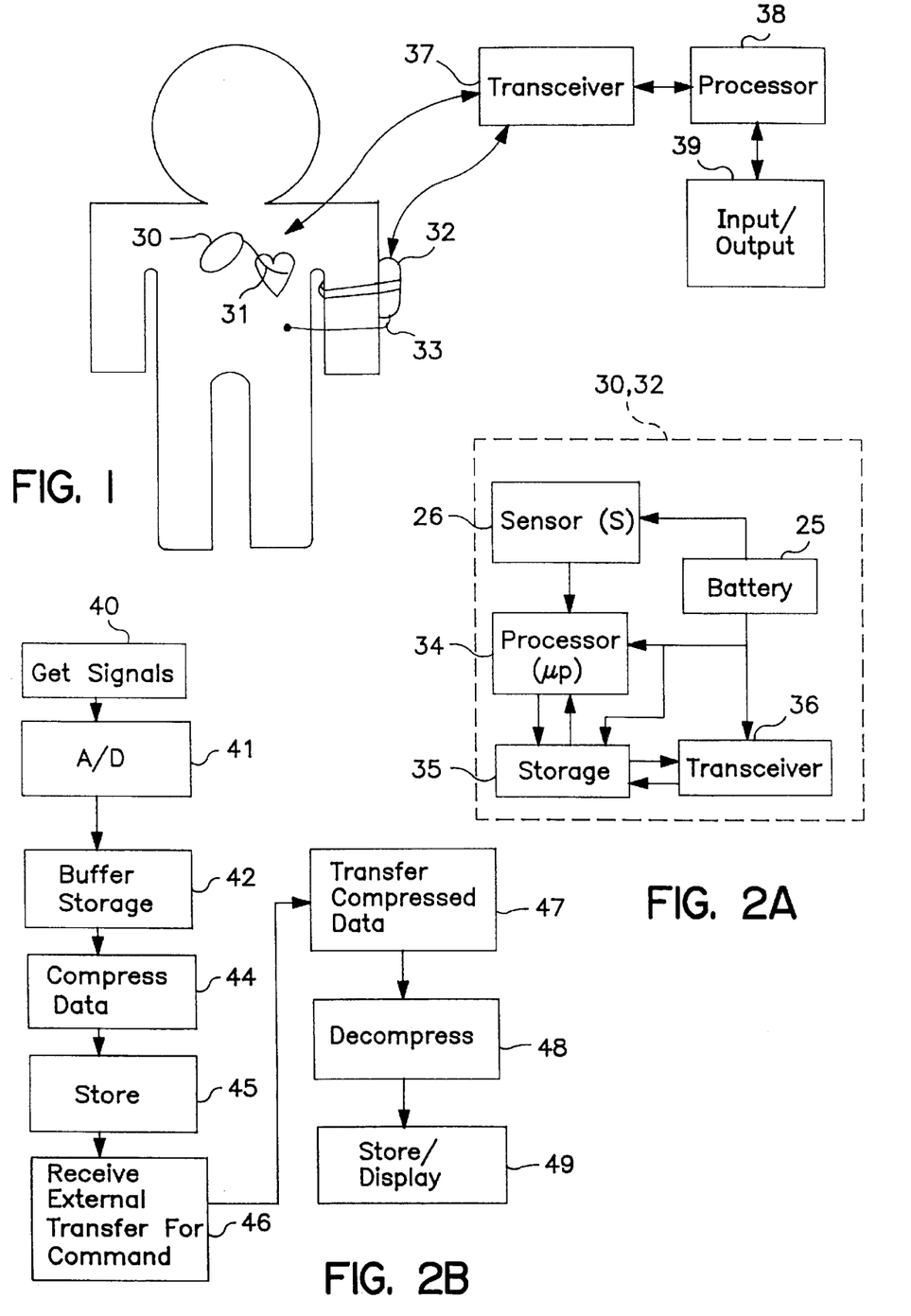
FIG. 1 is a diagram representing two forms of devices to which the invention is applicable, namely an implantable device such as a pacemaker, and a battery powered device worn on the outside of a patient.
FIG. 2A is a simple block diagram representing the major elements of an implantable or wearable device in accordance with this invention.
FIG. 2B is a simple flow diagram representing the major steps taken in compressing, transferring and decompressing data in accordance with this invention.

Referring now to FIG. 1, a diagram is shown illustrating the environment of the apparatus and method of this invention. The invention may be used with an implantable device such as a pacemaker 30, illustrated as implanted within a patient. Connected to the pacemaker is a lead 31, which extends into the patient heart, and has one or more electrodes at the distal end thereof which deliver stimulus pulses and also sense intracardiac or epicardial signals. As is well known in the pacemaker art, the sense signals can be received by the pacemaker, digitized and stored in memory, for later transmission to an external device 37. As shown, the transceiver 37 may be a conventional programmer as used in the pacemaker art. The programmer, when it has received data from the pacemaker, can transfer to a processor 38, which in turn can output data to input/output device 39, all in a well known manner. As is well known, implantable devices such as pacemakers cannot handle vast amounts of data, because of obvious limitations on power and memory capacity.

Also illustrated in FIG. 1 is a wearable device 32, shown strapped to the arm of a patient. Such device 32 may operate in conjunction, for example, with electrodes 33, for determining a patient ECG. As with the implanted device, data collected in battery powered device 32 can be downloaded to another device for further processing and outputting. The same restrictions on processing and memory availability may apply to such a battery powered wearable device.

Referring now to FIG. 2A, there is shown a simple block diagram representing the major elements of an implantable or wearable device in accordance with this invention. A battery 25 powers a sensor or sensors 26, which include leads 31 or 33. The sensor block may also include an amplifier stage and digitizing circuitry of conventional form. The digitized data is transmitted to processor block 34, which suitably contains a microprocessor. It is to be understood that the processing steps encompassed in this invention may be undertaken with any desired combination of dedicated hardware and/or software. The microprocessor is in communication with memory or storage, as shown at 35; the memory in turn is in communication with transceiver 36, for transmitting data to outside apparatus or receiving data and/or instructions therefrom.

Referring now to FIG. 2B, there is shown a simple flow diagram representing the major steps taken in compressing, transferring and decompressing data in accordance with this invention. At 40, the signals, such as EKG signals, are picked up in analog form. The analog signals are transformed into digital data at 41, and initial encoding steps can be taken at this point. The digital data is stored in buffer storage 42. At block 44, the data is compressed in accordance with the technique of this invention, and stored at block 45. At 46, a command to transfer data is received from an external source, indicating the availability to receive stored data. The compressed data is transferred at 47, in a conventional manner as is well known in the pacemaker art. At 48, the data is decompressed at the external device, to recreate in the original signals in digital form. The signal data is then stored at 49, or displayed.

Figure 3A:
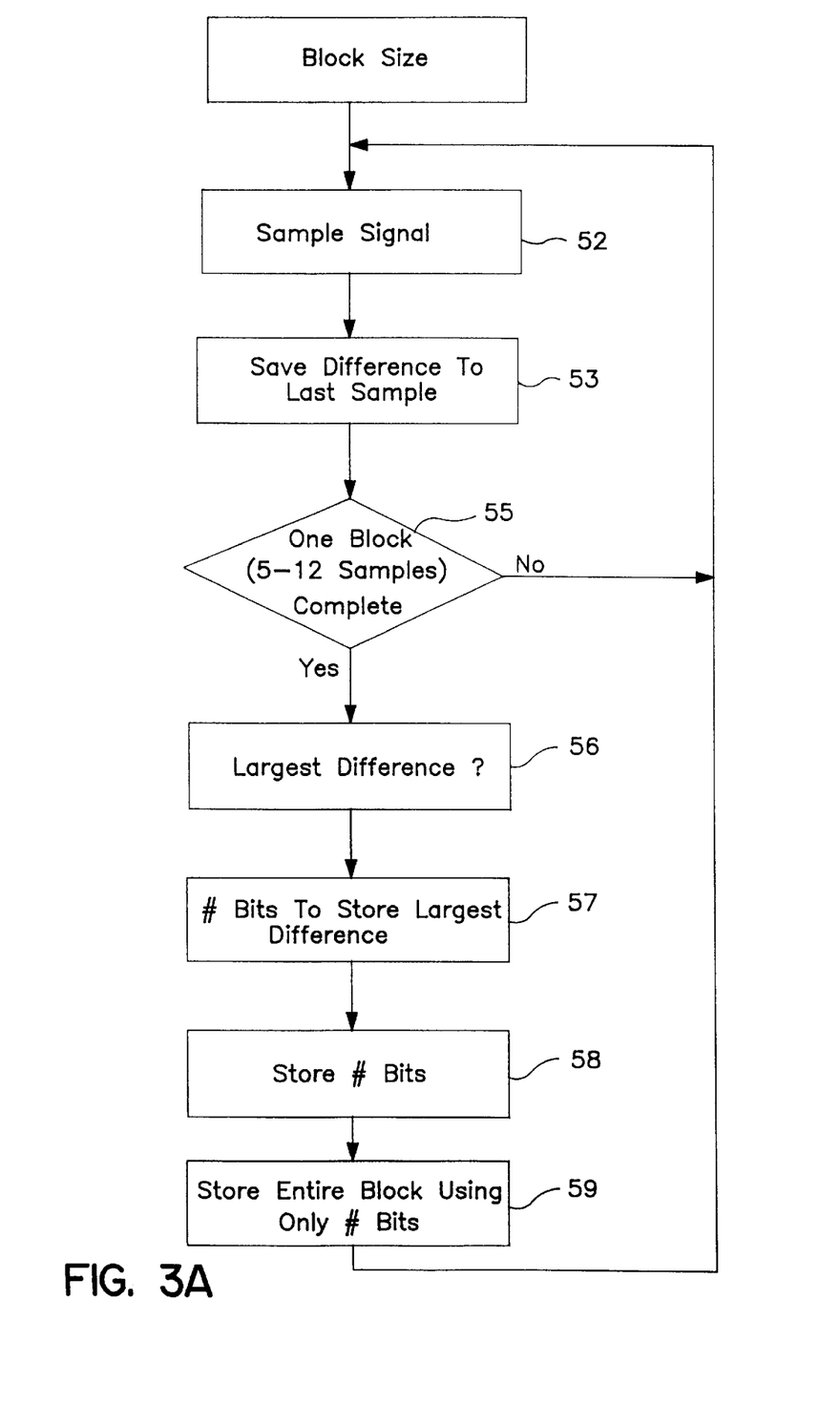
FIG. 3A is a flow diagram showing the basic steps taken in data compression in accord with this invention.

Referring now to FIG. 3A, there is shown a flow diagram illustrating the basic steps for data compression in accordance with this invention. At 51, BlockSize data is determined, having been stored in data through programming. At 52, the analog signal is sampled. Each such sample is compared to the last sample, and a difference or delta value is determined and saved, a shown in 53. Following this, at 55 it is determined whether a block of samples has been processed. Such block may be on the order of 5–12, which has been determined to be an optimal range for ECG and similar medical signals. It is to be understood that block size is to be determined in accordance with the nature of the application, since block size may be greater in the event of certain signals which exhibit lesser time variations. If the block has not been completed, the routine loops back to 52, and obtains the next sample. Only when all of the samples have been obtained, and the delta values corresponding to each have been determined and saved, does the routine proceed to block 56. At this point, it determines the largest difference, or the delta value with the highest absolute magnitude. Then, at 57, the routine determines the number of bits required to store the determined maximum delta. This value, # bits, is stored as shown in 58. Following this, the entire block of delta values is then stored sequentially in memory, using only a number of bits for each delta value corresponding to # bits. Thus, if # bits=5, and the block contains ten samples, then 50 bits are stored serially in memory corresponding to the ten delta values. Serial storage provides for the uninterrupted used of memory. Following this, the next block of data is processed in the same manner, continuing until all of the signal data has been processed.

Figure 3B:
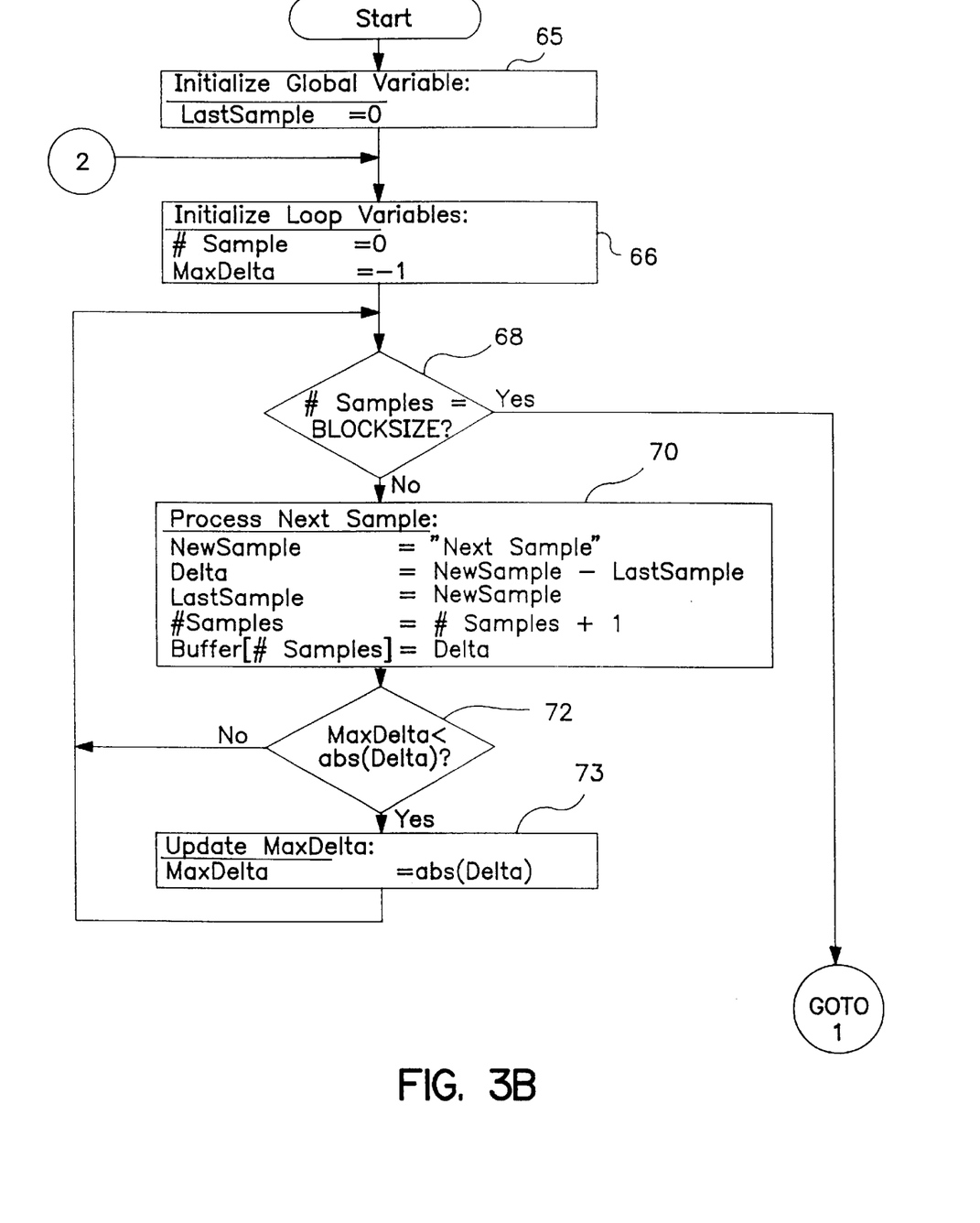
FIGS. 3B and 3C are flow diagrams representing in more detail the steps taken in accordance with this invention to compress data.
Figure 3C:
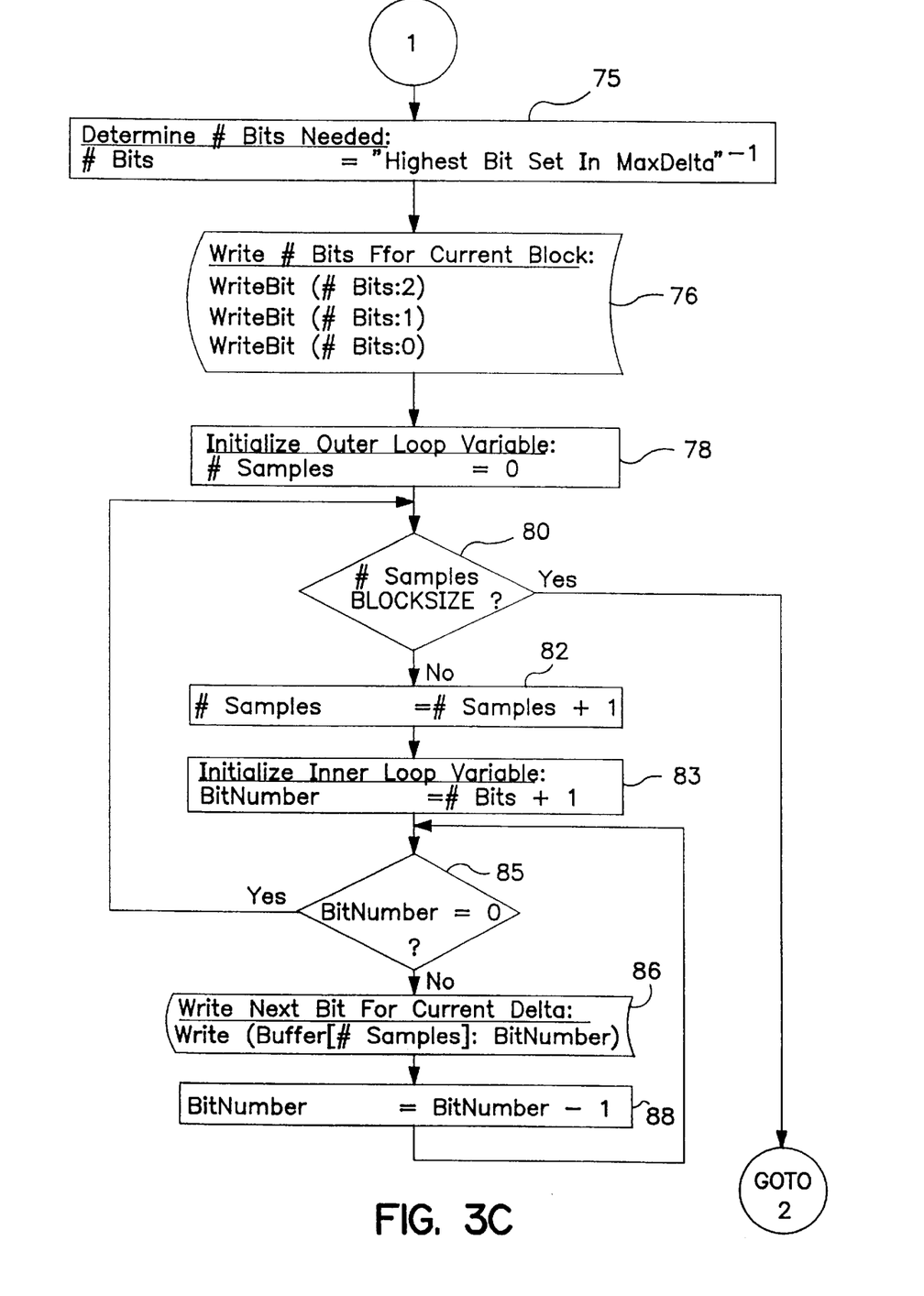

Referring now to FIGS. 3B and 3C, there is seen a flow diagram representing in greater detail the steps taken in accordance with this invention to compress data. At 65, a variable termed "LastSample" is set equal to zero, i.e., the value of the last sample is presumed to be a base value of zero. Following this, at 66, the variable # samples is set equal to zero, and the value MaxDelta is equal to −1. The routine then goes to 68, where it is determined if # samples equals BlockSize, i.e., have all the samples in the block been processed in this loop? If no, the routine goes to block 70, and obtains and processes the next sample. As shown at 70, the new sample is set equal to "NextSample"; delta is calculated as NewSample−LastSample; LastSample is then set equal to NewSample; # samples is set equal to # samples+1; and the delta value is placed in the buffer memory corresponding to the number of the sample. Then, at 72, it is determined whether the existing value of MaxDelta is less than the absolute value of delta that has thus far been obtained. If no, the routine goes back to block 68. However, if the answer at 72 is yes, this means that the absolute value of the latest determined delta is greater than the previously stored value of MaxDelta, and at 73 MaxDelta is updated to be set equal to the just obtained absolute value of delta. The routine then goes back to 68, and iterates until # samples equals block size. At this point, the value of MaxDelta and the deltas have been computed for all the samples in the block, and the routine goes to (1) as indicated.

As indicated at block 75 in FIG. 3C, # bits is determined as the highest bit set in MaxDelta. This can be done in any number of ways, e.g., using a priority decoder, calculating $\log_2$MaxDelta; or counting the number of right shifts of MaxDelta until MaxDelta reaches zero. Following this, at 76, the value of # bits for the current block is written. As noted at 76, this can be written as a 3-bit word for any application such as standard pacemakers that deal with signals of 8 bit resolution. Of course, if 16 bit resolution is used, then a 4-bit word is required. At 78, the outer loop variable # samples is initialized to zero. At 80, it is determined whether # samples equals BlockSize. Assuming the answer is no, at 82 # samples is incremented to # samples+1. Then, at 83, the inner loop variable Bit Number is set equal to # bits+1. This ensures that not only the significant number of bits is stored, but also one additional bit indicating the sign of the current delta. In particular, for each delta the sign bit is stored first, Next the absolute value of the delta is stored using only the calculated number of bits. During decompression this sign bit is read before the delta value. At 85, it is determined whether Bit Number equals zero. If yes, the routine branches back to 80; if no, the routine goes to 86 and writes the next bit for the current delta. Thus, for the delta corresponding to # samples, the current bit number is taken and written into memory. Following this, at 88, bit # is decremented by 1, and the routine loops back to 85. When the bit # is down to zero, the routine loops back to block 80 and, assuming that # samples does not yet equal block size, resets # samples and Bit Number, and loops again through inner loop 85, 86 and 88. When # samples is found to be equal to block size, the routine exits back to (2) of FIG. 3A, and starts again with another block.

Figure 4:
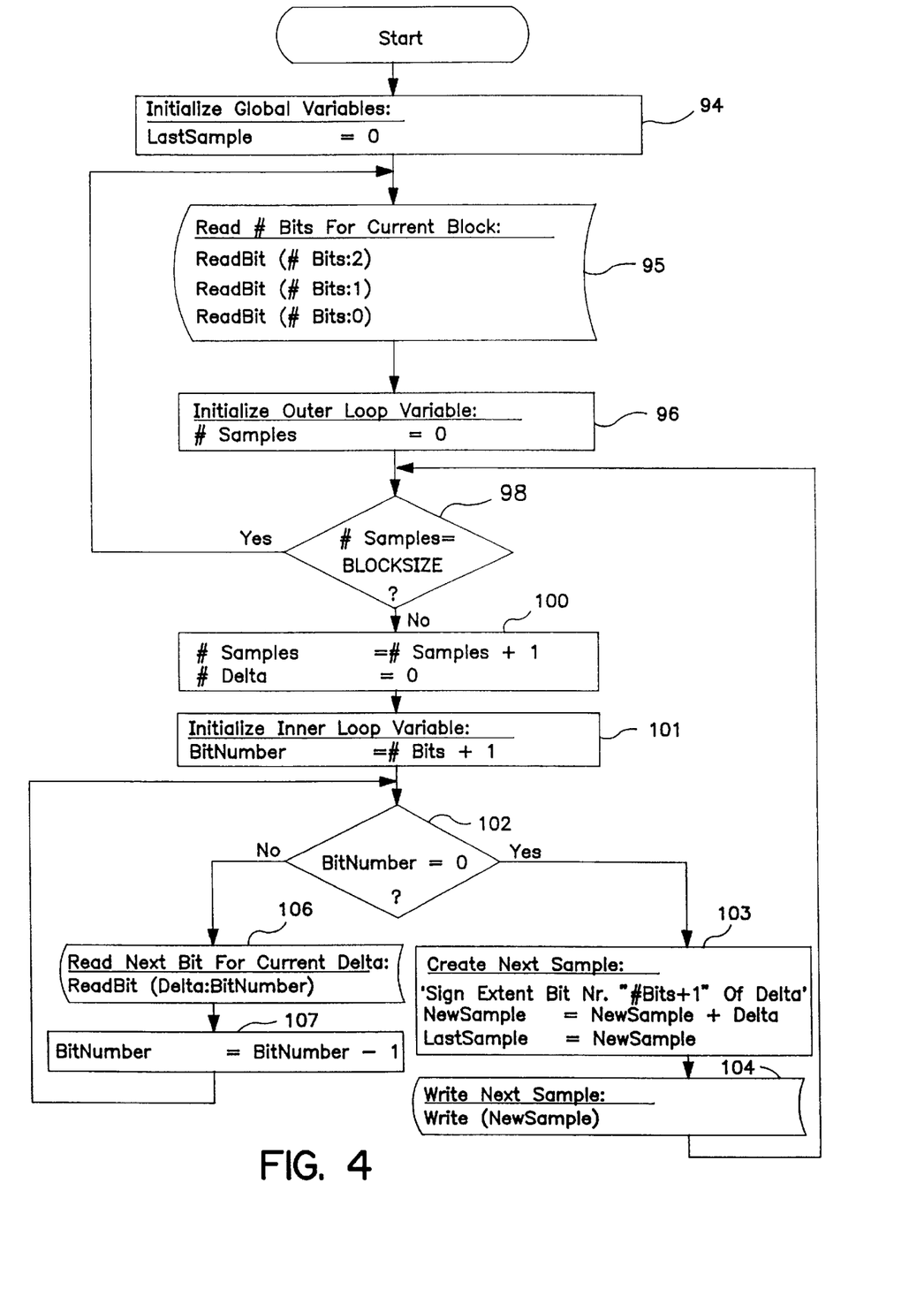
FIG. 4 is a flow diagram representing the steps taken in accordance with this invention to decompress data.

Referring now to FIG. 4, there is shown a flow diagram of the routine for decompressing the data. As seen at 94, variable LastSample is initialized at zero. At 95, # bits is read for the current block, i.e., each of the 3 bits is read to determine the number of bits being used. Following this, at 96 # samples is initialized to zero. At 98, it is determined whether # samples equals block size. If yes, the routine goes back to 95, to commence decompression of the next block. However, if no, the routine goes to 100 and sets # samples equal to # samples+1; and delta equal to zero. At 101, the inner loop variable Bit Number is initialized to # bits+1. In particular, for each delta the sign bit is stored first and next the absolute value of this delta is stored using only the calculated number of bits. During decompression, this sign bit is read before the delta. At 102, it is determined whether Bit Number equals zero. If no, the routine goes to 106 and reads the next bit for the current delta. Then at 107 Bit Number is set equal to Bit Number−1, and the routine loops back to 102. When Bit Number has been reduced to zero, the routine branches from 102 to 103, and creates the next sample. This is done by first doing a sign extend of the sign bit of delta, i.e. if the initial delta value was +7 and # bits was 3, the code 0111 would have been stored, while if the initial delta value was −7 the code 1001 would have been stored, in a two's complement notation. A two's complement notation is preferred to handle negative numbers but is not necessary. Performing the sign extend will create 8 bit deltas of 0000 0111 (binary +7) resp.1111 1001 (binary −7) and thus makes sure that the correct deltas, both positive and negative are reconstructed. With this reconstructed delta, the next sample is created by setting NewSample equal to LastSample+delta, and LastSample is set equal to NewSample. Then at 104, the "NextSample" is written as "NewSample". Following this, the routine goes back to block 98, and processes the NextSample. This is iterated until, at 98, the number of samples is determined to be equal to BlockSize, at which point the routine goes back to 95 for processing of the next block.

Figure 5:
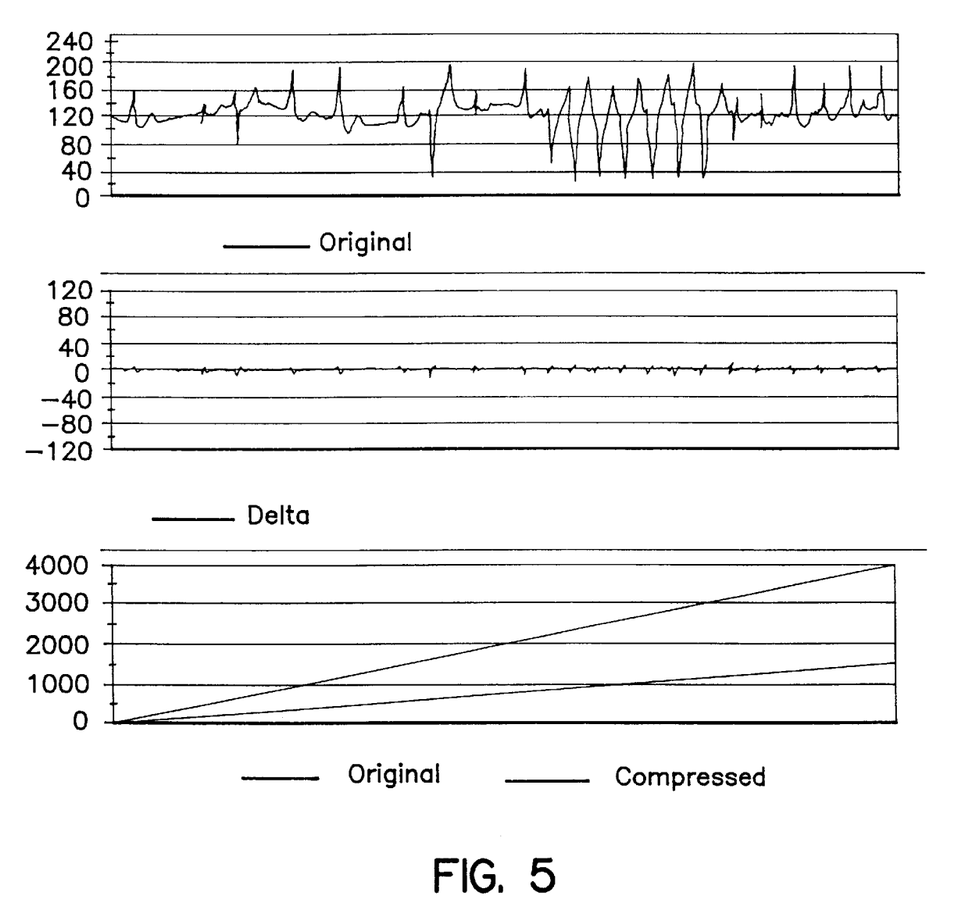
FIG. 5 is a series of graphs illustrating an example of an analog physiological signal, the delta reconstruction (time derivative) of the signal, and the bits needed for the original signal and for the compressed signal.

Referring to FIG. 5, there are shown three graphs, illustrating the efficiency of the compression technique of this invention. The top graph represents an analog signal which is representative of a signal obtained by a medical device. The middle graph represents delta values for the analog signal, illustrating that for many medical applications, the delta signals are much reduced in amplitude variations. The bottom graph of FIG. 5 represents cumulative the number of bits required to store the signal, for the original signal (top curve) and the compressed signal (bottom curve). As illustrated, the data compression of this invention provides a bit reduction of about 50%. This is achieved with relatively little processing, making it an extremely advantageous technique for applications where there are severe limitations on the available memory and battery power.

There is thus disclosed a method and system for providing data compression in low power environments, i.e., applications such as implantable stimulators or battery-driven devices. The advantages provided are good compression; minimal processing requirements; and full reconstruction of the original signal at time of decompression.

What is claimed is:

1. A method of data compression for use in storing data in, and transferring data from, an implantable medical device, comprising:

obtaining a physiological signal from a patient;

sampling said signal to obtain samples in the form of digital data;

selecting a block size corresponding to a selected number of samples per block; and for each block, comparing each sample in said block with the prior sample and determining a delta representative of the difference between said each sample and the prior sample, and saving each said delta; examining said delta signals and determining the largest absolute value; determining the number of bits required to store said largest delta, and storing said number of bits, and storing each said delta for said block using said number of bits.

2. The method of claim 1, comprising using said method to process and store data representative of ECG signals, and selecting said block size to be in the range of 5–12 samples.

3. The method of claim 1, comprising initializing before starting compression of a signal, by setting a zero value for an assumed last sample prior to the first sample of said signal.

4. The method of claim 1, comprising storing said number of bits and said bits representing each delta serially in memory storage, so as to provide uninterrupted use of memory.

5. The method of claim 4, further in combination with decompressing said stored data, said decompressing comprising reading said number of bits, determining each said stored delta, and algebraically adding said each delta to the value of the prior sample to recreate the samples and the signal.

6. A battery powered device, said device having means for obtaining physiological signals from a patient, memory for storing data representative of said signals, and means for transmitting said data to another device, further comprising:

sampling means for sampling said signals in time sequence, means for holding block data representative of a selected number of samples making a block, delta means operative for determining a delta for each sample, said delta being representative of the difference between said each sample and the prior sample, max bit means for determining, for each block, the maximum number of bits required for the largest delta of the block, and for storing max bit data representative of said number, for each said block, block means for storing in said memory delta data for each of said deltas of a block, each said delta data comprising said maximum number of bits, and said delta data for a block being stored together with said max bit data for said block, and repeat means for repeating the functions of determining max bit data and storing max bit data and delta data for each block of said signal, thereby storing compressed data representative of said signal.

7. The battery powered device as described in claim 6 in combination with an external device, said battery powered device further comprising receive means for receiving a transfer command from said external device, and transfer means for transferring said compressed data to said external device in response to said transfer command.

8. The battery powered device as described in claim 6, comprising block receive means for receiving said block data.

9. The battery powered device as described in claim 6, wherein said max bit means comprises means for storing said max bit data in a predetermined number of bit corresponding to the signal resolution of said device.

10. The device as described in claim 6, wherein said block means comprises means for storing said data continuously in said memory.

11. A method of data compression used in a battery powered device, said device having means for obtaining physiological signals from a patient, means for transforming said physiological signals into digital signals, and memory for storing data representative of said physiological signals, said method being used for compressing said digital signals prior to storing same in said memory, said method comprising:

determining a delta value for each of a series of said digital signals, each said delta value being representative of the difference between a digital signal and the prior digital signal,     examining said delta values and determining therefrom the largest of said delta values,     determining the number of bits required to represent said largest delta value in order to provide a predetermined resolution,     storing in said memory data representative of said determined number of bits, and storing delta values for each said digital signal in said series, each said delta value being represented by said determined number of bits.

12. The method as described in claim 11, comprising limiting said series to a predetermined number of said digital signals.

13. The method as described in claim 11, comprising limiting said series to 5–12 successive digital signals.

14. A method of operating an implantable medical device comprising the steps of:

obtaining a physiological signal from a patient;

sampling said signal to obtain samples in the form of digital data;

selecting a block size corresponding to a selected number of samples per block; and     for each block, comparing each sample in said block with the prior sample and determining a delta representative of the difference between said each sample and the prior sample, and saving each said delta; examining said delta signals and determining the largest absolute value; determining the number of bits required to store said largest delta, and storing said number of bits, and storing each said delta for said block using said number of bits whereby the total number of bits required to store or transfer the obtained physiological signal is reduced.

15. The method of claim 14, comprising using said method to process and store data representative of ECG signals, and selecting said block size to be in the range of 5–12 samples.

16. The method of claim 14, comprising initializing before starting compression of a signal, by setting a zero value for an assumed last sample prior to the first sample of said signal.

17. The method of claim 14, comprising storing said number of bits and said bits representing each delta serially in memory storage, so as to provide uninterrupted use of memory.

18. The method of claim 17, further in combination with decompressing said stored data, said decompressing comprising reading said number of bits, determining each said stored delta, and algebraically adding said each delta to the value of the prior sample to recreate the samples and the signal.

19. The method of claim 14, wherein said step of obtaining a physiological signal from a patient comprises obtaining ECG signals and selecting said block size to be in the range of 5–12 samples.

20. A method of data compression for use in storing data in, and transferring data from, an implantable medical device, comprising:

obtaining a physiological signal from a patient;

sampling said signal to obtain samples in the form of digital data;

selecting a block size corresponding to a selected number of samples per block; and     for each block, comparing each sample in said block with the prior sample and determining a delta representative of the difference between said each sample and the prior sample, and saving each said delta; examining said delta signals and determining the largest absolute value; determining the number of bits required to store said largest delta, and storing said number of bits, and storing each said delta for said block using said number of bits in a serial fashion in a memory of the implantable medical device so as to provide uninterrupted use of the memory.

\* \* \* \* \*